(12) United States Patent
Nisler et al.

(10) Patent No.: US 9,993,002 B2
(45) Date of Patent: Jun. 12, 2018

(54) 1,2,3-THIADIAZOL-5YL-UREA DERIVATIVES, USE THEREOF FOR REGULATING PLANT SENESCENCE AND PREPARATIONS CONTAINING THESE DERIVATIVES

(71) Applicant: USTAV EXPERIMENTALNI BOTANIKY AV CR, V.V.I., Praha 6—Lysolaje (CZ)

(72) Inventors: Jaroslav Nisler, Olomouc (CZ); Marek Zatloukal, Sumperk (CZ); Lukas Spichal, Olomouc (CZ); Radoslav Koprna, Olomouc (CZ); Karel Dolezal, Hlubocky (CZ); Miroslav Strnad, Olomouc (CZ)

(73) Assignees: USTAV EXPERIMENTALNI BOTANIKY AV CR, V.V.I., Lysolaje (CZ); UNIVERZITA PALACKEHO V OLOMOUCI, Olomouc (CZ)

( * ) Notice: Subject to any disclaimer, the term of this patent is extended or adjusted under 35 U.S.C. 154(b) by 0 days. days.

(21) Appl. No.: 15/506,127

(22) PCT Filed: Sep. 2, 2015

(86) PCT No.: PCT/CZ2015/050003
§ 371 (c)(1),
(2) Date: Feb. 23, 2017

(87) PCT Pub. No.: WO2016/037595
PCT Pub. Date: Mar. 17, 2016

(65) Prior Publication Data
US 2017/0280721 A1     Oct. 5, 2017

(30) Foreign Application Priority Data

Sep. 9, 2014    (CZ) ................................ PV2014-613
Apr. 2, 2015    (CZ) ................................ PV2015-230

(51) Int. Cl.
| | | |
|---|---|---|
| A01N 47/36 | (2006.01) |
| C07D 285/06 | (2006.01) |
| C07D 417/12 | (2006.01) |
| A01N 25/04 | (2006.01) |
| A01N 25/08 | (2006.01) |
| A01N 25/12 | (2006.01) |
| A01N 25/14 | (2006.01) |
| A01N 25/22 | (2006.01) |
| A01N 25/30 | (2006.01) |
| A01N 25/02 | (2006.01) |

(52) U.S. Cl.
CPC ............. *A01N 47/36* (2013.01); *A01N 25/02* (2013.01); *A01N 25/04* (2013.01); *A01N 25/08* (2013.01); *A01N 25/12* (2013.01); *A01N 25/14* (2013.01); *A01N 25/22* (2013.01); *A01N 25/30* (2013.01); *C07D 285/06* (2013.01); *C07D 417/12* (2013.01)

(58) Field of Classification Search
CPC .... C07D 285/06; C07D 417/12; A01N 47/36; A01N 25/02; A01N 25/04; A01N 25/08; A01N 25/12; A01N 25/14; A01N 25/22; A01N 25/30
See application file for complete search history.

(56) References Cited

U.S. PATENT DOCUMENTS 3,883,547 A * 5/1975 Schulz ................. C07D 285/06
                                                     504/225
4,294,605 A * 10/1981 Arndt .................. C07D 285/06
                                                     504/170

FOREIGN PATENT DOCUMENTS

WO         0205638 A1     1/2002

OTHER PUBLICATIONS

Wing-Kin Yip and Shang Fa Yang, "Effect of Thidiazuron, a Cytokinin-Active Urea Derivative, in Cytokinin-Dependent Ethylene Production Systems", Plant Physiology (1986) 80, 515-519.*
International Search Report and Written Opinion of corresponding PCT Appln. No. PCT/CZ2015/050003, dated Jan. 22, 2016.

* cited by examiner

*Primary Examiner* — John D Pak
*Assistant Examiner* — Nathan W Schlientz
(74) *Attorney, Agent, or Firm* — Notaro, Michalos & Zaccaria P.C.

(57) ABSTRACT

Substituted 1,2,3-thiadiazol-5yl-urea derivatives, their use as anti-senescence and anti-stress factors of plant cells, organs and the whole plant, and preparations containing these derivatives.

18 Claims, 1 Drawing Sheet

1,2,3-THIADIAZOL-5YL-UREA DERIVATIVES, USE THEREOF FOR REGULATING PLANT SENESCENCE AND PREPARATIONS CONTAINING THESE DERIVATIVES

TECHNICAL FIELD

The invention relates to substituted 1,2,3-thiadiazol-5yl-urea derivatives, their use as antistress compounds, in regulating plant senescence and aging of plant organs and cells, and preparations containing these derivatives.

BACKGROUND ART

Stressed-induced senescence is nowadays a major problem from agro-economic point of view and endangers food security, worldwide. Only few types of compounds providing antisenescent and/or antioxidant properties are known, many of them are showing also undesirable side effects, such as inhibition of root growth (purine-based compounds such as 6-benzylaminopurine (BAP), zeatin), etc. Therefore, provision of new classes of substances with strong antistress properties, not showing these undesirable side effects, is needed.

It is an object of this invention to provide urea derivatives having improved selectivity and efficiency index in the inhibition of plant senescence and stress-induced symptoms, without undesirable inhibitory effects to root development.

DISCLOSURE OF THE INVENTION

The object of this invention is use of 1,2,3-thiadiazol-5-yl-urea derivatives of the general formula (I),

I wherein
R1 is selected from the group consisting of
C$_1$-C$_6$ alkyl, substituted with at least one moiety selected from hydroxy, C$_1$-C$_4$ alkoxy, thio, C$_1$-C$_4$ alkylthio, cyano and halogen;
C$_2$-C$_6$ alkenyl, optionally substituted with at least one moiety selected from hydroxy, C$_1$-C$_4$ alkoxy, thio, C$_1$-C$_4$ alkylthio, cyano and halogen;
C$_2$-C$_6$ alkynyl, optionally substituted with at least one moiety selected from hydroxy, C$_1$-C$_4$ alkoxy, thio, C$_1$-C$_4$ alkylthio, cyano and halogen;
tetrahydro-furan-2-yl-methyl or tetrahydro-furan-3-yl-methyl, optionally substituted with at least one moiety selected from hydroxy, C$_1$-C$_4$ alkyl, C$_1$-C$_4$ alkoxy, thio, C$_1$-C$_4$ alkylthio, cyano and halogen;
thiophen-2-yl-methyl or thiophen-3-yl-methyl optionally substituted with at least one moiety selected from hydroxy, C$_1$-C$_4$ alkyl, C$_1$-C$_4$ alkoxy, thio, C$_1$-C$_4$ alkylthio, cyano and halogen;
furan-2-yl-methyl or furan-3-yl-methyl, optionally substituted with at least one moiety selected from hydroxy, C$_1$-C$_4$ alkyl, C$_1$-C$_4$ alkoxy, thio, C$_1$-C$_4$ alkylthio, cyano and halogen;
1,3-dioxolan-2-yl-methyl, optionally substituted with at least one moiety selected from hydroxy, C$_1$-C$_4$ alkyl, C$_1$-C$_4$ alkoxy, thio, C$_1$-C$_4$ alkylthio, cyano and halogen;
tetrahydropyran-2-ylmethyl, tetrahydropyran-3-ylmethyl or tetrahydropyran-4-ylmethyl, optionally substituted with at least one moiety selected from hydroxy, C$_1$-C$_4$ alkyl, C$_1$-C$_4$ alkoxy, thio, C$_1$-C$_4$ alkylthio, cyano and halogen;
(3,4-dihydro-2H-pyran-2-yl)methyl, (3,4-dihydro-2H-pyran-3-yl)methyl, (3,4-dihydro-2H-pyran-4-yl)methyl, (3,4-dihydro-2H-pyran-5-yl)methyl or (3,4-dihydro-2H-pyran-6-yl)methyl, optionally substituted with at least one moiety selected from hydroxy, C$_1$-C$_4$ alkyl, C$_1$-C$_4$ alkoxy, thio, C$_1$-C$_4$ alkylthio, cyano and halogen;

as antistress compounds and/or for inhibiting senescence and/or oxidative damage in plants, plant organs and plant cells, and/or for increasing the yield of plants, without the side effect of root growth inhibition.

Another object of the present invention are 1,2,3-thiadiazol-5-yl-urea derivatives of the general formula (Ia), Ia wherein
R1a is selected from the group consisting of
C$_1$-C$_6$ alkyl, substituted with at least one moiety selected from hydroxy, C$_1$-C$_4$ alkoxy, thio, C$_1$-C$_4$ alkylthio, cyano and halogen;
C$_2$-C$_6$ alkenyl, optionally substituted with moiety selected from hydroxy, C$_1$-C$_4$ alkoxy, thio, C$_1$-C$_4$ alkylthio, cyano and halogen;
C$_2$-C$_6$ alkynyl, optionally substituted moiety selected from hydroxy, C$_1$-C$_4$ alkoxy, thio, C$_1$-C$_4$ alkylthio, cyano and halogen;
tetrahydro-furan-2-yl-methyl or tetrahydro-furan-3-yl-methyl, optionally substituted with at least one moiety selected from hydroxy, C$_1$-C$_4$ alkyl, C$_1$-C$_4$ alkoxy, thio, C$_1$-C$_4$ alkylthio, cyano and halogen;
thiophen-2-yl-methyl or thiophen-3-yl-methyl optionally substituted with at least one moiety selected from hydroxy, C$_1$-C$_4$ alkyl, C$_1$-C$_4$ alkoxy, thio, C$_1$-C$_4$ alkylthio, cyano and halogen;
furan-2-yl-methyl or furan-3-yl-methyl, substituted with at least one moiety selected from hydroxy, C$_1$-C$_4$ alkyl, C$_1$-C$_4$ alkoxy, thio, C$_1$-C$_4$ alkylthio, cyano and halogen;
1,3-dioxolan-2-yl-methyl, optionally substituted with at least one moiety selected from hydroxy, C$_1$-C$_4$ alkyl, C$_1$-C$_4$ alkoxy, thio, C$_1$-C$_4$ alkylthio, cyano and halogen;
tetrahydropyran-2-ylmethyl, tetrahydropyran-3-ylmethyl or tetrahydropyran-4-ylmethyl, optionally substituted with at least one moiety selected from hydroxy, C$_1$-C$_4$ alkyl, C$_1$-C$_4$ alkoxy, thio, C$_1$-C$_4$ alkylthio, cyano and halogen;
(3,4-dihydro-2H-pyran-2-yl)methyl, (3,4-dihydro-2H-pyran-3-yl)methyl, (3,4-dihydro-2H-pyran-4-yl)methyl, (3,4-dihydro-2H-pyran-5-yl)methyl or (3,4-dihydro-2H-pyran-6-yl)methyl, optionally substituted with at least one moiety selected from hydroxy, C$_1$-C$_4$ alkyl, C$_1$-C$_4$ alkoxy, thio, C$_1$-C$_4$ alkylthio, cyano and halogen.

Preferably, when R1 and/or R1a is alkyl, alkenyl or alkynyl, these groups are substituted at terminal atom with at least one moiety selected from hydroxy, $C_1$-$C_4$ alkyl, $C_1$-$C_4$ alkoxy, thio, $C_1$-$C_4$ alkylthio, cyano and halogen.

Preferably, R1 and/or R1a is furan-2-yl-methyl or furan-3-yl-methyl or 2-methoxyethyl.

The generic substituent groups have meanings as defined herein below, wherein alkyl denotes branched or linear alkyl group;

alkenyl denotes branched or linear hydrocarbon chain with at least one double bond;

alkynyl denotes branched or linear hydrocarbon chain with at least one triple bond;

halogen is selected from the group comprising fluorine, bromine, chlorine and iodine atom;

cyano denotes the group —CN;

hydroxy denotes the group —OH;

alkyloxy denotes the group —O-alkyl, preferably, alkyloxy is methyloxy or ethyloxy; thio denotes the group —SH;

alkylthio group denotes to —S-alkyl, preferably, alkylthio is methylthio or ethylthio.

When the compounds of this invention contain a chiral centre, then all enantiomers, mixtures of enantiomers and racemates fall within the framework of the present invention. The present invention is further meant to include the compounds of general formula I when they are in the form of salts with alkali metals, ammonium or amines, as well as in the form of addition salts with acids.

Preferably, R1 and/or R1a is selected from 2-hydroxy-ethyl, 3-hydroxy-propyl, 4-hydroxy-butyl, 5-hydroxy-pentyl, 6-hydroxy-hexyl, 2-methoxy-ethyl, 3-methoxy-propyl, 4-methoxy-butyl, 5-methoxy-pentyl, 6-methoxy-hexyl, 2-ethoxy-ethyl, 3-ethoxy-propyl, 4-ethoxy-butyl, 5-ethoxy-pentyl, 6-ethoxy-hexyl, 2,2-dimethoxy-ethyl, 1,2-dimethoxy-ethyl, 1,2,2-trimethoxy-ethyl, 3,3-dimethoxy-propyl, (E)-4-hydroxy-3-methyl-but-2-enyl, (Z)-4-hydroxy-3-methyl-but-2-enyl, 3-methyl-but-2-enyl, isopentenyl, 2-hydroxy-propyl, 2-hydroxy-1-methyl-ethyl, 2-methoxy-propyl, 2-methoxy-1-methyl-ethyl, 3,3-dimethoxy-1-methyl-propyl, 3,3-dimethoxy-2-methyl-propyl, 2,3,3-trimethoxy-propyl, 4,4-dimethoxy-butyl, 3,4,4-trimethoxy-butyl, 2-thio-ethyl, 3-thio-propyl, 4-thio-butyl, 5-thio-pentyl, 6-thio-hexyl, 2-methylthio-ethyl, 3-methylthio-propyl, 4-methylthio-butyl, 5-methylthio-pentyl, 6-methylthio-hexyl, 2-ethylthio-ethyl, 3-ethylthio-propyl, 4-ethylthio-butyl, 5-ethylthio-pentyl, 6-ethylthio-hexyl, vinyl, allyl, but-3-enyl, Pent-4-enyl, Hex-5-enyl, Ethynyl, Prop-2-ynyl, But-3-ynyl, Pent-4-ynyl, Hex-5-ynyl, (Z)-Buta-1,3-dienyl, (1Z, 3E)-Penta-1,3-dienyl, (E)-Penta-2,4-dienyl, (1Z,3E)-Hexa-1,3,5-trienyl, (2E,4E)-Hexa-2,4-dienyl, (E)-Hexa-3,5-dienyl, 2-chloro-ethyl, 3-chloro-propyl, 4-chloro-butyl, 5-chloro-pentyl, 6-chloro-hexyl, 2-bromo-ethyl, 3-bromo-propyl, 4-bromo-butyl, 5-bromo-pentyl, 6-bromo-hexyl, tetrahydro-furan-2-yl-methyl, thiophen-2-yl-methyl, furan-2-yl-methyl, (5-methyl-furan-2-yl)-methyl, 1,3-dioxolan-2-yl-methyl, tetrahydropyran-2-yl-methyl, 3,4-dihydro-2H-pyran-2-yl-methyl, 4-hydroxy-3-methylbutyl, (Z)-1'-methyl-4-hydroxy-3-methylbut-2-enyl, (E)-1'-methyl-4-hydroxy-3-methylbut-2-enyl, furan-2-yl-methyl, furan-3-yl-methyl, 2-methoxyethyl.

In another preferred embodiment, the compound of general formula (I) and/or (Ia) is selected from:

1-(2-hydroxy-ethyl)-3-[1,2,3]thiadiazol-5-yl-urea, 1-(3-hydroxy-propyl)-3-[1,2,3]thiadiazol-5-yl-urea, 1-(4-hydroxy-butyl)-3-[1,2,3]thiadiazol-5-yl-urea, 1-(5-hydroxy-pentyl)-3-[1,2,3]thiadiazol-5-yl-urea, 1-(6-hydroxy-hexyl)-3-[1,2,3]thiadiazol-5-yl-urea, 1-(2-methoxy-ethyl)-3-[1,2,3]thiadiazol-5-yl-urea, 1-(3-methoxy-propyl)-3-[1,2,3]thiadiazol-5-yl-urea, 1-(4-methoxy-butyl)-3-[1,2,3]thiadiazol-5-yl-urea, 1-(5-methoxy-pentyl)-3-[1,2,3]thiadiazol-5-yl-urea, 1-(6-methoxy-hexyl)-3-[1,2,3]thiadiazol-5-yl-urea, 1-(2-ethoxy-ethyl)-3-[1,2,3]thiadiazol-5-yl-urea, 1-(3-ethoxy-propyl)-3-[1,2,3]thiadiazol-5-yl-urea, 1-(4-ethoxy-butyl)-3-[1,2,3]thiadiazol-5-yl-urea, 1-(5-ethoxy-pentyl)-3-[1,2,3]thiadiazol-5-yl-urea, 1-(6-ethoxy-hexyl)-3-[1,2,3]thiadiazol-5-yl-urea, 1-(2,2-dimethoxy-ethyl)-3-[1,2,3]thiadiazol-5-yl-urea, 1-(1,2-dimethoxy-ethyl)-3-[1,2,3]thiadiazol-5-yl-urea, 1-[1,2,3]thiadiazol-5-yl-3-(1,2,2-trimethoxy-ethyl)-urea, 1-(3,3-dimethoxy-propyl)-3-[1,2,3]thiadiazol-5-yl-urea, 1-((E)-4-hydroxy-3-methyl-but-2-enyl)-3-[1,2,3]thiadiazol-5-yl-urea, 1-(3-methyl-but-2-enyl)-3-[1,2,3]thiadiazol-5-yl-urea, 1-(2-hydroxy-propyl)-3-[1,2,3]thiadiazol-5-yl-urea, 1-(2-hydroxy-1-methyl-ethyl)-3-[1,2,3]thiadiazol-5-yl-urea, 1-(2-methoxy-propyl)-3-[1,2,3]thiadiazol-5-yl-urea, 1-(2-methoxy-1-methyl-ethyl)-3-[1,2,3]thiadiazol-5-yl-urea, 1-(3,3-dimethoxy-1-methyl-propyl)-3-[1,2,3]thiadiazol-5-yl-urea, 1-(3,3-dimethoxy-2-methyl-propyl)-3-[1,2,3]thiadiazol-5-yl-urea, 1-[1,2,3]thiadiazol-5-yl-3-(2,3,3-trimethoxy-propyl)-urea, 1-(4,4-Dimethoxy-butyl)-3-[1,2,3]thiadiazol-5-yl-urea, 1-[1,2,3]Thiadiazol-5-yl-3-(3,4,4-trimethoxy-butyl)-urea, 1-(2-thio-ethyl)-3-[1,2,3]thiadiazol-5-yl-urea, 1-(3-thio-propyl)-3-[1,2,3]thiadiazol-5-yl-urea, 1-(4-thio-butyl)-3-[1,2,3]thiadiazol-5-yl-urea, 1-(5-thio-pentyl)-3-[1,2,3]thiadiazol-5-yl-urea, 1-(6-thio-hexyl)-3-[1,2,3]thiadiazol-5-yl-urea, 1-(2-methythio-ethyl)-3-[1,2,3]thiadiazol-5-yl-urea, 1-(3-methythio-propyl)-3-[1,2,3]thiadiazol-5-yl-urea, 1-(4-methythio-butyl)-3-[1,2,3]thiadiazol-5-yl-urea, 1-(5-methythio-pentyl)-3-[1,2,3]thiadiazol-5-yl-urea, 1-(6-methythio-hexyl)-3-[1,2,3]thiadiazol-5-yl-urea, 1-(2-ethylthio-ethyl)-3-[1,2,3]thiadiazol-5-yl-urea, 1-(3-ethylthio-propyl)-3-[1,2,3]thiadiazol-5-yl-urea, 1-(4-ethylthio-butyl)-3-[1,2,3]thiadiazol-5-yl-urea, 1-(5-ethylthio-pentyl)-3-[1,2,3]thiadiazol-5-yl-urea, 1-(6-ethylthio-hexyl)-3-[1,2,3]thiadiazol-5-yl-urea, 1-vinyl-3-[1,2,3]thiadiazol-5-yl-urea, 1-allyl-3-[1,2,3]thiadiazol-5-yl-urea, 1-but-3-enyl-3-[1,2,3]thiadiazol-5-yl-urea, 1-pent-4-enyl-3-[1,2,3]thiadiazol-5-yl-urea, 1-hex-5-enyl-3-[1,2,3]thiadiazol-5-yl-urea, 1-ethynyl-3-[1,2,3]thiadiazol-5-yl-urea, 1-prop-2-ynyl-3-[1,2,3]thiadiazol-5-yl-urea, 1-but-3-ynyl-3-[1,2,3]thiadiazol-5-yl-urea, 1-pent-4-ynyl-3-[1,2,3]thiadiazol-5-yl-urea, 1-hex-5-ynyl-3-[1,2,3]thiadiazol-5-yl-urea, 1-(4-hydroxy-3-methylbutyl)-3-[1,2,3]thiadiazol-5-yl-urea, 1-((E)-1'-methyl-4-hydroxy-3-methylbut-2-enyl)-3-[1,2,3]thiadiazol-5-yl-urea, 1-((Z)-buta-1,3-dienyl)-3-[1,2,3]thiadiazol-5-yl-urea, 1-((1Z,3E)-Penta-1,3-dienyl)-3-[1,2,3]thiadiazol-5-yl-urea, 1-((E)-penta-2,4-dienyl)-3-[1,2,3]thiadiazol-5-yl-urea, 1-((1Z,3E)-Hexa-1,3,5-trienyl)-3-[1,2,3]thiadiazol-5-yl-urea, 1-((2E,4E)-Hexa-2,4-dienyl)-3-[1,2,3]thiadiazol-5-yl-urea, 1-((E)-hexa-3,5-dienyl)-3-[1,2,3]thiadiazol-5-yl-urea, 1-(2-chloro-ethyl)-3-[1,2,3]thiadiazol-5-yl-urea, 1-(3-chloro-propyl)-3-[1,2,3]thiadiazol-5-yl-urea, 1-(4-chloro-butyl)-3-[1,2,3]thiadiazol-5-yl-urea, 1-(5-chloro-pentyl)-3-[1,2,3]thiadiazol-5-yl-urea, 1-(6-chloro-hexyl)-3-[1,2,3]thiadiazol-5-yl-urea, 1-(2-bromo-ethyl)-3-[1,2,3]thiadiazol-5-yl-urea, 1-(3-bromo-propyl)-3-[1,2,3]thiadiazol-5-yl-urea, 1-(4-bromo-butyl)-3-[1,2,3]thiadiazol-5-yl-urea, 1-(5-bromo-pentyl)-3-[1,2,3]thiadiazol-5-yl-urea, 1-(6-bromo-hexyl)-3-[1,2,3]thiadiazol-5-yl-urea, 1-(2,2-dichloro-ethyl)-3-[1,2,3]thiadiazol-5-yl-urea, 1-(3,3-dichloro-propyl)-3-[1,2,3]thiadiazol-5-yl-urea, 1-(4,4-dichloro-butyl)-3-[1,2,3]thiadiazol-5-yl-urea, 1-(5,5-dichloro-pentyl)-3-[1,2,3]thiadiazol-5-yl-urea, 1-(6,6-dichloro-hexyl)-3-[1,2,3]thiadiazol-5-yl-urea, 1-(2,2-dibromo-ethyl)-3-[1,2,3]thiadiazol-5-yl-urea, 1-(3,3-dibromo-propyl)-3-[1,2,3]

thiadiazol-5-yl-urea, 1-(4,4-dibromo-butyl)-3-[1,2,3]thiadiazol-5-yl-urea, 1-(5,5-dibromo-pentyl)-3-[1,2,3]thiadiazol-5-yl-urea, 1-(6,6-dibromo-hexyl)-3-[1,2,3]thiadiazol-5-yl-urea, 1-(2-methoxy-ethyl)-1-methyl-3-[1,2,3]thiadiazol-5-yl-urea, 1,1-bis-(2-methoxy-ethyl)-3-[1,2,3]thiadiazol-5-yl-urea, 1,1-bis-(3-methoxy-propyl)-3-[1,2,3]thiadiazol-5-yl-urea, 1,1-bis-(2-chloro-ethyl)-3-[1,2,3]thiadiazol-5-yl-urea, 1,1-bis-(2-bromo-ethyl)-3-[1,2,3]thiadiazol-5-yl-urea, 1,1-bis-(2-hydroxy-ethyl)-3-[1,2,3]thiadiazol-5-yl-urea, 1,1-bis-(2-thio-ethyl)-3-[1,2,3]thiadiazol-5-yl-urea, 1,1-bis-(2-methylthio-ethyl)-3-[1,2,3]thiadiazol-5-yl-urea, 1-(tetrahydro-furan-2-yl-methyl)-3-[1,2,3]thiadiazol-5-yl-urea, 1-(thiophen-2-yl-methyl)-3-[1,2,3]thiadiazol-5-yl-urea, 1-(furan-2-yl-methyl)-3-[1,2,3]thiadiazol-5-yl-urea, 1-(5-methyl-furan-2-yl-methyl)-3-[1,2,3]thiadiazol-5-yl-urea, 1-(1,3-dioxolan-2-yl-methyl)-3-[1,2,3]thiadiazol-5-yl-urea, 1-(tetrahydropyran-2-yl-methyl)-3-[1,2,3]thiadiazol-5-yl-urea, 1-(3,4-dihydro-2H-pyran-2-yl-methyl)-3-[1,2,3]thiadiazol-5-yl-urea, 1-(furan-2-yl-methyl)-3-[1,2,3]thiadiazol-5-yl-urea, 1-(furan-3-yl-methyl)-3-[1,2,3]thiadiazol-5-yl-urea, 1-(2-methoxyethyl)-3-[1,2,3]thiadiazol-5-yl-urea.

The compounds of the present invention do not show the undesirable inhibitory activity to root growth which is typical for other antisenescent compounds (in particular cytokinins) of the prior art. Even at high concentrations the negative effect on root growth is not present at all or this negative effect is strongly suppressed. Furthermore, the compounds of the present invention do not show the undesirable defoliating activity typical for thidiazuron (TDZ) and hitherto known derivatives thereof.

The compounds of the present invention can be applied to whole plants, plant organs or plant cells, e.g., in tissue cultures. They are especially suitable for use in tissue cultures because they do not exhibit the inhibitory effect on growth and division of plant cells at high concentrations and show minimum toxicity for these cells compared to other antisenescent compounds known in the prior art. This enables their use in broad concentration range without negative effects.

A further aspect of the invention is preferably the use of 1,2,3-thiadiazol-5-yl-urea derivatives of the general formula I, for delaying chlorophyll degradation and senescence of plant tissues. This positive effect is related to the unique effect of these derivatives on the peroxidation of membrane lipids. The 1,2,3-thiadiazol-5-yl-urea derivatives of the present invention function as inhibitors of membrane lipid peroxidation, which further increases their anti-senescence and anti-stress activity.

A further aspect of the invention is the use of substituted 1,2,3-thiadiazolyl-urea derivatives of the general formula I as inhibitors of stress and stress-induced senescence in the production of crops, in particular cereals (wheat, barley, rice, maize, rye, oat, sorghum, and related species), beet (sugar beet and fodded beet); pomes, drupes and soft fruits (apples, pears, plums, peaches, almonds, cherries, strawberries and blackberries); leguminous plants (beans, lentils, peas, soybeans); oil plants (rape, mustard, poppy, olives, sunflowers, coconut, *Ricinus*, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, cinnamomum, camphor) or plants such as tobacco, nuts, eggplants, sugar cane, tea, vine gpapes, hops, bananas and natural rubber and medicinal plants, as well as ornamentals. Crops include those which have been rendered tolerant towards classes of growth factors by conventional breeding methods or genetic engineering methods. The weeds to be controlled can be both monocotyledonous and dicotyledonous weeds, for example *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanbthium, Amaranthus, Chenopodium, Ipomoena, Chrysanthemum, Galium, Viola* and *Veronica*.

The stress can be in particular a stress caused by dryness and/or heat or cold and/or salinity (salinity stress).

The invention further includes antisenescent and/or antistress preparations for plants, plant organs and plant cells, comprising at least one compound of the general formula (Ia) and at least one auxiliary substance.

The invention further encompasses a method of inhibiting stress and/or senescence and/or oxidative damage in plants, plant organs and/or plant cells, and/or for increasing the yield of plants, without the side effect of root growth inhibition, comprising the step of applying at least one compound of the general formula (I) onto said plant, plant organ and/or plant cell.

The compounds of the present invention can be prepared by processes known to a chemist of ordinary skill. Preferably, they may be prepared by a method in which 1,2,3-thiadiazol-5-ylisocyanate is prepared by a convential method (Kurita K. and Iwakura Y., J. Org. Chem. 41, 2070-71 (1976)) from 1,2,3-thiadiazol-5-ylamine and diphosgene. 1,2,3-Thiadiazol-5-ylisocyanate is then allowed to react with a corresponding amine to give the desired product.

The compounds of the general formula I are used in unmodified form or, preferably, together with excipients conventionally employed in the art of preparations. To this end they are conveniently formulated as concentrates of active compounds as well as suspensions and dispersions, preferentially isotonic water solutions, suspensions and dispersion, diluted emulsions, soluble powders, dusts, granulates, creams, gels, oil suspensions and also encapsulations, e.g. polymeric substances. As with the type of the preparation, the methods of application, such as spraying, atomizing, dusting, scattering, coating or pouring, are chosen in accordance with the intended objectives and the prevailing circumstances. The preparations may be sterilized and/or contain further excipients of neutral nature such as preservatives, stabilizers, wetting agents or emulgators, solubilizing agents, as well as fertilizers, micronutrient donors or other formulations for obtaining special effects.

Preparations

The preparations comprising the compounds of general formula I (active ingredients) and, where appropriate, one or more solid or liquid excipients, are prepared in a manner known per se e.g. by mixing and/or grinding the active ingredients with excipients, e.g. solvents or solid carriers. In addition, surface-active compounds (surfactants) may also be used in the preparations.

Depending on the nature of the compound of general formula I to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, in WO 97/34485.

Also suitable in the preparation of the compositions containing compounds derived from substituted 1,2,3-thiadiazolyl-urea derivatives of the general formula I according to the invention are the surfactants conventionally used in formulation technology, which are described, inter alia, in "McCutcheon's Detergents and Emulsifiers Annual" MC Publishing Corp., Ridgewood N.J., 1981; Stache, H., "Tensid-Taschenbuch", Carl Hanser Verlag, Munich, 1981; and M. and J. Ash, "Encyclopedia of Surfactants", Vol. 1-3, Chemical Publishing Co., New York, 1980-81.

The formulation of the preparation containing compounds usually contains from 0.1 to 95% active ingredient by weight, from 5 to 99.9% by weight of solid or liquid adjuvants or pharmaceutical carriers, depending on the application method, and from 0.1 to 25% by weight of a surfactant.

Whereas commercial products are usually formulated as concentrates, the end user will normally employ dilute formulations. The compositions may also comprise further ingredients, such as stabilisers, e.g. vegetable oils or epoxidised vegetable oils (epoxidised coconut 0; 1, rapeseed oil or soybean oil), antifoams, e.g. silicone oil, preservatives, stabilizers, wetting agents or emulsifiers, viscosity factors, binders, tackifiers, and also fertilisers or other active ingredients. Preferred formulations have especially the following compositions: (%=percent by weight)

Emulsifiable Concentrates:
active ingredient mixture: 1 to 90%, preferably 5 to 20%
surfactant: 1 to 30%, preferably 10 to 20%
liquid carrier: 5 to 94%, preferably 70 to 85%
Dusts:
active ingredient mixture: 0.1 to 10%, preferably 0.1 to 5%
solid carrier: 99.9 to 90%, preferably 99.9 to 95%
Suspension Concentrates:
active ingredient mixture: 5 to 75%, preferably 10 to 50%
water: 94 to 24%, preferably 88 to 30%
surfactant: 1 to 40%, preferably 2 to 30%
Wettable Powders:
active ingredient mixture: 0.5 to 90%, preferably 1 to 80%
surfactant: 0.5 to 20%, preferably 1 to 15%
solid carrier: 5 to 95%, preferably 15 to 90%
Granules:
active ingredient mixture: 0.1 to 30%, preferably 0.1 to 15%
solid carrier: 99.9 to 70%, preferably 99.9 to 85%

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of the compounds of general formula I, or of compositions comprising them, in the protection of crop plants against the damaging effects of growth regulators, various methods and techniques come into consideration, such as, for example, the following:

i) Seed Dressing a) Dressing of the seeds with a wettable powder formulation of a compound of the general formula I by shaking in a vessel until uniformly distributed over the seed surface (dry dressing). In that procedure approximately from 1 to 500 g of compound of the general formula I (4 g to 2 kg of wettable powder) are used per 100 kg of seed.

b) Dressing of the seeds with an emulsifiable concentrate of a compound of formula I according to method a) (wet dressing).

c) Dressing by immersing the seeds for from 1 to 72 hours in a liquor comprising from 100 to 1000 ppm of a compound of general formula I and preferably subsequently drying the seeds (immersion dressing).

Dressing the seeds or treating the germinated seedlings are naturally the preferred methods of application, because treatment with the active ingredients is directed entirely at the target crop. Generally from 1 to 1000 g of antidote, preferably from 5 to 250 g of antidote, are used per 100 kg of seed, but depending on the methodology, which also enables the addition of other active ingredients or micronutrients, the concentration limits indicated can be varied up or down (repeat dressing).

ii) Application as a Tank Mixture

A liquid formulation is used in the amount of 0.005 to 5.0 kg per hectare. Such tank mixtures are applied before or after sowing.

iii) Application to the Seed Furrow

The compounds of formula I are introduced into the open, sown seed furrow in the form of an emulsifiable concentrate, wettable powder or granules. Once the seed furrow has been covered over, the growth regulator is applied in the usual manner in the pre-emergence process.

iv) Controlled Release of Active Ingredient

The compounds of formula I are applied in solution to mineral granule carriers or polymerised granules (urea/formaldehyde) and dried. If desired, it is also possible to apply a coating that allows the active ingredient to be released in metered amounts over a specific period of time (coated granules).

EXAMPLES OF CARRYING OUT THE INVENTION

The starting material for the compounds of the formula I or Ia is 1,2,3-thiadiazol-5-yl-amine, which was obtained from TCI Europe. The 1,2,3-thiadiazol-5-ylamine was converted to the 5-isocyanato-1,2,3-thiadiazole by stirring the 1,2,3-thiadiazol-5-yl-amine with excessive amount of diphosgene in THF. The compounds of the formula I or Ia can be then prepared by mild heating of 5-isocyanato-1,2,3-thiadiazole and the corresponding amine (commercially available from Sigma Aldrich, Olchemim, TCI Europe) in the presence of catalytic amount of triethylamine in THF. The amines of compounds having hydroxyl group were protected by t-BDMSiCl prior to condensation with 5-isocyanato-1,2,3-thiadiazole; deprotection was carried out in propanolic HCl, all according to (Greene TW and Wuts PGM; Protective Groups in Organic Synthesis 3rd ed., New York, (1991)).

Elemental analyses (C, H and N) were performed on an EA1108 CHN analyser (Fissons Instruments). The melting points were determined on a BÜCHI Melting Point B-540 apparatus and are uncorrected. Analytical thin layer chromatography (TLC) was carried out using silica gel 60 $WF_{254}$ plates (Merck), solvent $CHCl_3$:MeOH:conc. $NH_4OH$ (8:2:0.2, v/v/v). ES+ mass spectra were recorded using direct probe on Waters ZMD 2000 mass spectrometer. The mass monitoring interval was 10 to 1500 amu. The spectra were collected using 3.0 second cyclical scans and applying sample cone voltage 25 V at source block temperature 150° C., desolvation temperature 80° C. and desolvation gas flow rate 200 l/hour. The mass spectrometer was directly coupled to a MassLynx data system. NMR spectra were measured in a Jeol 500 SS spectrometer operating at a temperature of 300 K and a frequency of 500.0 MHz ($^1H$) and 75.48 MHz ($^{13}C$), respectively. Samples were prepared by dissolving the compounds in DMSO-$d_6$. Tetramethylsilane (TMS) was used as the internal standard.

Example 1

Preparation of 5-isocyanato-1,2,3-thiadiazole

The synthesis of isocyanates from amines was described elsewhere (Kurita K. and Iwakura Y., J. Org. Chem. 41, 2070-71 (1976)). In detail, 1,2,3-Thiadiazol-5-yl amine (1.01 g, 10 mmol) was dissolved in THF (40 mL) and added dropwise into a solution of diphosgene (2.6 g, 13 mmol) in THF (100 mL). Reaction mixture was stirred for 40 minutes at −10° C.; then the reaction mixture was shortly heated to 30° C. After heating, solvent and excess of diphosgene were evaporated. The yellow solid residue was 5-isocyanato-1,2,3-thiadiazole, which was re-suspended in diethyl ether and filtered off. Yield: 95%, $^1H$ NMR (6, ppm, DMSO-$d_6$): 7.75 (1H, s, CH).

Example 2

Preparation of 1-(2-Hydroxy-propyl)-3-[1,2,3]thiadiazol-5-yl-urea (25)

1-Amino-propan-2-ol (0.097 g; 1.3 mmol) was mixed with THF (10 mL) and the triethylamin (0.262 g; 2.6 mol) and trimethylsylil chloride (0.209 g; 1.9 mmol) was added. Mixture was stirred in laboratory temperature for 24 hours. Then triethylamonium chloride was filtered off and mother liquers was evaporated. The 2-trimethylsilanyloxy-propylamine (0.13 g) was used without further analysis. 5-Isocyanato-1,2,3-thiadiazole (111.8 mg; 0.88 mmol) was mixed with 2-trimethylsilanyloxy-propylamine (130 mg; 0.88 mmol) in THF (10 ml) and catalytic amount of triethylamine. Reaction mixture was stirred at 60° C. for 24 hours in high pressure tube. TLC ($CHCl_3$: MeOH, 4:1) indicated total conversion of starting compounds to O-protected urea. Solvent was replaced by 5 mL of 2-propanol and the deprotection by 5-6 M HCl in 2-propanol (3 mL) was carried out. The mixture was allowed to stir 17 hours. Solvent was evaporated and residue was suspended in water (10 mL). Product was extracted by ethylacetate (4×4 mL). Ethylacetate was replaced by diethylether and the white crystal was filtered off. Yield: 63 mg white substance (35.2%). TLC (chloroform-methanol; 4:1): one single spot; free of the starting material, HPLC purity: 98+%. $^1H$ NMR (DMSO-$d_6$): 2.95-3.01 (1H, m, $CH_2$), 3.10-3.16 (1H, m, $CH_2$), 1.00 (3H, d, J=6.11, $CH_3$), 3.66 (1H, heptet, J=6.72, CH), 4.78 (1H, d, J=4.28, OH), 6.91 (1H, s (br), NH), 8.46 (1H, s, CH), 10.64 (1H, s, NH).

Example 3

Preparation of 1-(2-Chloro-ethyl)-3-[1,2,3]thiadiazol-5-yl-urea (65)

5-Isocyanato-1,2,3-thiadiazole (0.127 g; 0.001 mol) was mixed with 2-chloro-ethylamine hydrochloride (0.116 g; 0.001 mol) in DCM (10 ml) and triethylamine (0.151 g; 0.0015). The reaction mixture was stirred at 50° C. for 24 hours. After cooling to room temperature the triethylamonium chloride was removed from reaction mixture by water extraction (3×2 mL). The DCM layer was dried over $MgSO_4$ and then the solvent was evaporated. Residuum was resuspended in diethylether and yellow precipitate was filtered off. Yield: 0.13 g white substance (63.1%). TLC (chloroform-methanol; 9:1): one single spot; free of the starting material, HPLC purity: 98+%. $^1H$ NMR (DMSO-$d_6$): 3.45 (2H, q, J=6.30, $CH_2$), 3.65 (2H, q, J=6.30, $CH_2$), 7.24 (1H, t, J=6.30, NH), 8.47 (1H, s, CH), 10.87 (1H, s, NH).

Example 4

Preparation of 1-(2,2-dimethoxy-ethyl)-3-[1,2,3]thiadiazol-5-yl-urea (16)

5-Isocyanato-1,2,3-thiadiazole (0.127 g; 0.001 mol) was mixed with 2,2-Dimethoxy-ethylamine (0.105 g; 0.001 mol) in THF (6 ml) and catalytic amount of triethylamine. The reaction mixture was stirred at 60° C. for 24 hours. After cooling to room temperature the solvent was evaporated and the residue was dissolved in DCM and triturated by diethylether. The white precipitate was filtered off. Yield: 0.151 g white substance (65.1%). TLC (chloroform-methanol; 9:1): one single spot; free of the starting material, HPLC purity: 98+%. $^1H$ NMR (DMSO-$d_6$): 3.36-3.39 (8H, m, CH2, 2×$CH_3$), 4.38 (1H, t, J=5.0, CH), 6.21 (1H, t, J=5.5, NH), 8.28 (1H, s, CH), 10.30 (1H, s (br), NH).

Example 5

Preparation of 1-Allyl-3-[1,2,3]thiadiazol-5-yl-urea (50)

5-Isocyanato-1,2,3-thiadiazole (127 mg; 1 mmol) was mixed with allylamine (57.1 mg; 1 mmol) in THF (6 ml) and catalytic amount of triethylamine. The reaction mixture was stirred at 60° C. for 24 hours. After cooling to room temperature the solvent was evaporated and the residue was purified by flash silica column chromatography (mobile phase CHCl3:MeOH, 9:1). Yield: 120 mg white substance (66.6%). TLC (chloroform-methanol; 9:1): one single spot; free of the starting material, HPLC purity: 98+%. $^1H$ NMR ($CDCl_3$-$d_1$): 3.75 (2H, d, J=5.15, $CH_2$), 4.97 (1H, d, J=10.31, $CH_2$), 5.04 (1H, d, J=17.18, $CH_2$), 5.68 (1H, octet, J1=5.15, J2=6.87, CH), 6.13 (1H, s (br), NH), 8.19 (1H, s (br), CH), 10.14 (1H, s (br), NH).

Example 6

Preparation of N-furfuryl-N'-1,2,3-thiadiazol-5-yl-urea (84)

5-Isocyanato-1,2,3-thiadiazole (1.27 g, 10 mmol) was dissolved in 100 mL THF. 100 µL triethylamine was added to this solution and furfurylamin (0.97 g, 10 mmol) in 20 mL THF was added dropwise at the temperature of 30° C. The mixture was reacted for 5 hours, THF was then evaporated using a rotary vacuum evaporator and 50 mL dichloromethane was added to the crude product. The precipitate was re-suspended and filtered off. Yield: 1.2 g; 53%, $^1$H NMR (6, ppm, DMSO-d6): 4.32 (2H, d, J=5.5 Hz, CH2), 6.24 (1H, d, J=4.0 Hz, ArH-furfuryl), 6.36 (1H, t, J=2.0 Hz, ArH-furfuryl), 7.52 (1H, t, J=5.5, NH), 7.56 (1H, d, J=4.0 Hz, ArH-furfuryl), 8.47 (1H, s, CH), 10.76 (1H, s (br), NH).

Example 7

Preparation of 1-(2-methoxy-ethyl)-3-[1,2,3]thiadiazol-5-yl-urea (6)

5-Isocyanato-1,2,3-thiadiazole (12.7 g; 0.1 mol) was mixed with 2-methoxy-ethylamine (7.51 g; 0.1 mol) in THF (600 ml) and catalytic amount of triethylamine (600 µL). The reaction mixture was stirred at 50° C. for 24 hours. After cooling to room temperature the solvent was evaporated to solid residue and the product was crystallized from ethanol. Precipitate was filtered off, washed with ether (2×100 mL) and dried in the drying oven at 60° C. into constant weight. Yield: 13.0 g white substance (64.3%). TLC (chloroform-methanol; 9:1): one single spot; free of the starting material, HPLC purity: 98+%. $^1$H NMR (DMSO-d$_6$): 3.22 (3H, s, CH$_3$), 3.28 (2H, t, J=5.73, CH$_2$), 3.36 (2H, t, J=5.15, CH$_2$), 7.03 (1H, t, J=5.73, NH), 8.45 (1H, s, CH), 10.67 (1H, s, NH).

TABLE 1

Compounds prepared by the method of examples 2-7

| No | R1 | % C (calc/found) | % H (calc/found) | % N (calc/found) | ES MS [M + H]⁺ |
|---|---|---|---|---|---|
| 1 | 2-hydroxy-ethyl | 31.9/32.2 | 4.3/4.4 | 30.0/30.3 | 189.3 |
| 2 | 3-hydroxy-propyl | 35.6/35.3 | 5.0/4.8 | 27.7/27.5 | 203.1 |
| 3 | 4-hydroxy-butyl | 38.9/38.4 | 5.6/5.7 | 25.9/26.2 | 217.1 |
| 4 | 5-hydroxy-pentyl | 41.7/42.0 | 6.1/6.3 | 24.3/24.5 | 231.3 |
| 5 | 6-hydroxy-hexyl | 44.3/44.5 | 6.6/6.8 | 23.0/22.8 | 245.1 |
| 6 | 2-methoxy-ethyl | 35.6/35.8 | 5.0/5.2 | 27.7/28.0 | 203.2 |
| 7 | 3-methoxy-propyl | 38.9/38.6 | 5.6/5.4 | 25.9/25.7 | 217.2 |
| 8 | 4-methoxy-butyl | 41.7/42.0 | 6.1/6.0 | 24.3/24.4 | 231.2 |
| 9 | 5-methoxy-pentyl | 44.3/44.1 | 6.6/6.6 | 23.0/23.3 | 245.1 |
| 10 | 6-methoxy-hexyl | 46.5/46.8 | 7.0/7.1 | 21.7/21.8 | 259.2 |
| 11 | 2-ethoxy-ethyl | 38.9/39.2 | 5.6/5.4 | 25.9/26.0 | 217.2 |
| 12 | 3-ethoxy-propyl | 41.7/41.8 | 6.1/6.1 | 24.3/24.5 | 231.2 |
| 13 | 4-ethoxy-butyl | 44.3/44.5 | 6.6/6.5 | 23.0/23.2 | 245.1 |
| 14 | 5-ethoxy-pentyl | 46.5/46.2 | 7.0/7.2 | 21.7/21.5 | 259.2 |
| 15 | 6-ethoxy-hexyl | 48.5/48.4 | 7.4/7.3 | 20.6/20.7 | 273.4 |
| 16 | 2,2-dimethoxy-ethyl | 36.2/36.5 | 5.2/5.3 | 24.1/23.8 | 233.3 |
| 17 | 1,2-dimethoxy-ethyl | 36.2/36.6 | 5.2/5.4 | 24.1/23.9 | 233.3 |
| 18 | 1,2,2-trimethoxy-ethyl | 36.6/36.4 | 5.4/5.3 | 21.4/21.6 | 263.3 |
| 19 | 3,3-dimethoxy-propyl | 39.0/39.3 | 5.7/5.6 | 22.8/22.7 | 246.3 |
| 20 | (E)-4-hydroxy-3-methyl-but-2-enyl | 42.1/42.0 | 5.3/5.5 | 24.5/24.8 | 229.3 |
| 21 | 3-methyl-but-2-enyl | 45.3/45.1 | 5.7/5.8 | 26.4/26.5 | 213.3 |
| 22 | isopentenyl | 45.3/45.0 | 5.7/5.7 | 26.4/26.8 | 213.3 |
| 23 | 4-hydroxy-3-methyl-butyl | 41.7/41.8 | 6.1/6.0 | 24.3/24.0 | 231.4 |
| 24 | (E)-1'-methyl-4-hydroxy-3-methylbut-2-enyl | 44.6/44.8 | 5.8/5.9 | 23.1/22.7 | 243.4 |
| 25 | 2-hydroxy-propyl | 35.6/35.9 | 5.0/4.8 | 27.7/27.4 | 203.1 |
| 26 | 2-hydroxy-1-methyl-ethyl | 35.6/35.8 | 5.0/5.1 | 27.7/7.5 | 203.2 |
| 27 | 2-methoxy-propyl | 38.9/38.7 | 5.6/5.4 | 25.9/26.2 | 217.2 |
| 28 | 2-methoxy-1-methyl-ethyl | 38.9/38.5 | 5.6/5.8 | 25.9/25.7 | 217.3 |
| 29 | 3,3-dimethoxy-1-methyl-propyl | 41.5/41.8 | 6.2/6.1 | 21.5/21.1 | 261.4 |
| 30 | 3,3-dimethoxy-2-methyl-propyl | 41.5/41.7 | 6.2/6.3 | 21.5/21.2 | 261.4 |
| 31 | 2,3,3-trimethoxy-propyl | 39.1/39.4 | 5.8/5.9 | 20.3/20.5 | 277.2 |
| 32 | 4,4-dimethoxy-butyl | 41.5/41 | 6.2/6.1 | 21.5/21.8 | 261.4 |
| 33 | 3,4,4-trimethoxy-butyl | 41.4/8 | 6.3/6.3 | 19.3/19.0 | 290.4 |
| 34 | 2-thio-ethyl | 29.4/29.5 | 4.0/4.1 | 27.4/27.8 | 205.3 |
| 35 | 3-thio-propyl | 33.0/33.2 | 4.6/4.5 | 25.7/25.5 | 218.4 |
| 36 | 4-thio-butyl | 36.2/36.1 | 5.2/5.3 | 24.1/24.3 | 233.4 |
| 37 | 5-thio-pentyl | 39.0/39.0 | 5.7/5.5 | 22.7/28.0 | 247.4 |
| 38 | 6-thio-hexyl | 41.5/41.6 | 6.2/6.0 | 21.5/21.5 | 261.2 |
| 39 | 2-methylthio-ethyl | 33.0/33.2 | 4.6/4.5 | 25.7/25.8 | 218.2 |
| 40 | 3-methylthio-propyl | 36.2/36.0 | 5.2/5.4 | 24.1/23.8 | 233.3 |
| 41 | 4-methylthio-butyl | 39.0/39.1 | 5.7/5.6 | 22.7/22.8 | 247.4 |
| 42 | 5-methylthio-pentyl | 41.5/41.5 | 6.2/6.3 | 21.5/21.2 | 261.3 |
| 43 | 6-methylthio-hexyl | 43.8/43.5 | 6.6/6.5 | 20.4/20.4 | 275.4 |
| 44 | 2-ethylthio-ethyl | 36.2/36.5 | 5.2/5.3 | 24.1/24.4 | 233.4 |
| 45 | 3-ethylthio-propyl | 39.0/38.6 | 5.7/5.6 | 22.7/22.9 | 247.4 |
| 46 | 4-ethylthio-butyl | 41.5/41.3 | 6.2/6.3 | 21.5/21.7 | 261.2 |
| 47 | 5-ethylthio-pentyl | 43.8/43.7 | 6.6/6.5 | 20.4/20.3 | 275.3 |
| 48 | 6-ethylthio-hexyl | 45.8/45.7 | 7.0/6.8 | 19.4/19.5 | 289.3 |
| 49 | vinyl | 35.3/35.5 | 3.5/3.4 | 33.0/33.0 | 171.3 |
| 50 | allyl | 39.1/39.4 | 4.4/4.5 | 30.4/30.2 | 185.3 |
| 51 | but-3-enyl | 42.4/42.6 | 5.1/5.2 | 28.3/28.6 | 199.1 |
| 52 | Pent-4-enyl | 45.3/45.3 | 5.7/5.8 | 26.4/26.7 | 213.4 |
| 53 | Hex-5-enyl | 47.8/47.7 | 6.2/6.0 | 24.8/25.0 | 227.4 |
| 54 | Ethynyl | 35.7/35.8 | 2.4/2.4 | 33.3/33.2 | 169.2 |
| 55 | Prop-2-ynyl | 39.5/39.8 | 3.3/3.4 | 30.8/30.9 | 183.3 |
| 56 | But-3-ynyl | 42.9/42.7 | 4.2/4.1 | 28.6/28.4 | 197.3 |
| 57 | Pent-4-ynyl | 45.7/45.6 | 4.8/4.6 | 26.7/26.6 | 211.3 |
| 58 | Hex-5-ynyl | 48.2/48.2 | 5.4/5.5 | 25.0/25.2 | 225.2 |
| 59 | (Z)-Buta-1,3-dienyl | 42.9/42.7 | 4.1/4.2 | 28.6/28.3 | 197.4 |
| 60 | (1Z,3E)-Penta-1,3-dienyl | 45.7/46.0 | 4.8/4.9 | 26.7/26.4 | 211.4 |
| 61 | (E)-Penta-2,4-dienyl | 45.7/45.9 | 4.8/5.0 | 26.7/26.4 | 211.4 |
| 62 | (1Z,3E)-Hexa-1,3,5-trienyl | 48.6/48.5 | 4.5/4.5 | 25.2/25.0 | 223.3 |
| 63 | (2E,4E)-Hexa-2,4-dienyl | 48.2/48.0 | 5.4/5.5 | 25.0/24.7 | 225.4 |
| 64 | (E)-Hexa-3,5-dienyl | 48.2/48.4 | 5.4/5.6 | 25.0/25.1 | 225.4 |
| 65 | 2-chloro-ethyl | 29.1/29.3 | 3.4/3.5 | 27.1/27.4 | 207.6 |
| 66 | 3-chloro-propyl | 32.7/32.5 | 4.1/4.0 | 25.4/25.5 | 221.8 |
| 67 | 4-chloro-butyl | 35.8/35.7 | 4.7/4.8 | 23.9/24.2 | 235.6 |
| 68 | 5-chloro-pentyl | 38.6/39.8 | 5.3/5.4 | 22.5/22.1 | 249.8 |
| 69 | 6-chloro-hexyl | 41.1/39.8 | 5.8/5.6 | 21.3/21.2 | 263.8 |
| 70 | 2-bromo-ethyl | 23.9/24.1 | 2.8/2.9 | 22.3/22.6 | 252.2 |
| 71 | 3-bromo-propyl | 27.2/27.5 | 3.4/3.5 | 21.1/21.0 | 266.2 |
| 72 | 4-bromo-butyl | 30.1/30.5 | 4.0/3.9 | 20.1/20.4 | 280.2 |
| 73 | 5-bromo-pentyl | 32.8/33.1 | 4.5/4.4 | 27.3/27.0 | 294.3 |
| 74 | 6-bromo-hexyl | 35.2/35.1 | 4.9/4.9 | 18.2/18.6 | 308.1 |
| 75 | tetrahydro-furan-2-yl-methyl | 42.1/42.0 | 5.3/5.4 | 24.5/24.3 | 229.1 |
| 76 | tetrahydro-furan-3-yl-methyl | 42.1/42.0 | 5.3/5.4 | 24.5/24.3 | 229.1 |
| 77 | furan-3-yl-methyl | 42.9/42.5 | 3.6/3.7 | 25.0/25.1 | 225.2 |
| 78 | thiophen-2-yl-methyl | 40.0/40.3 | 3.3/3.3 | 23.3/23.5 | 241.2 |
| 79 | (5-methyl-furan-2-yl)-methyl | 45.4/45.6 | 4.2/4.4 | 23.5/23.4 | 239.3 |
| 80 | 1,3-dioxolan-2-yl-methyl | 36.5/36.7 | 4.4/4.2 | 24.3/24.1 | 231.1 |
| 81 | tetrahydropyran-2-yl-methyl | 44.6/44.7 | 5.8/6.0 | 23.1/23.0 | 243.2 |
| 82 | 3,4-dihydro-2H-pyran-2-yl-methyl | 45.0/44.8 | 5.0/4.8 | 23.3/23.6 | 241.2 |
| 83 | (Z)-4-hydroxy-3-methyl-but-2-enyl | 42.1/42.3 | 5.3/5.4 | 24.5/24.5 | 229.2 |
| 84 | N-furfuryl | 42.9/43.2 | 3.6/3.7 | 25.0/24.8 | 225.3 |

Example 8

Anti-Senescent Activity of Novel Compounds Tested in Senescent Bioassay on Wheat Leaf Segments in the Dark Conditions Seeds of winter wheat, *Triticum aestivum* cv. Hereward, were washed under running water for 24 hours and then sown on perlite soaked with Hogland's solution. They were placed in the growth chamber at 25° C. with a 16/8 h light period at 50 µmol·m$^{-2}$·s$^{-1}$. After 7 days, the first leaf was fully developed and the second leaf had started to grow. A tip section of the first leaf, approximately 4 cm long, was removed from 4 seedlings and trimmed slightly to a combined weight of 100 mg. The basal ends of the four leaf tips were placed into the 96-wells plate containing 150 µL of the tested derivative solution each. The entire plate was inserted into a plastic box lined with paper tissues soaked in distilled water to prevent leaf sections from drying out. After 96 h incubation in the dark at 25° C., the leaves were removed and chlorophyll extracted by heating at 80° C. for 10 min in 5 mL of 80% ethanol (v/v). The sample volume was then restored to 5 mL by the addition of 80% ethanol (v/v). The absorbance of the extract was recorded at 665 nm. In addition, chlorophyll extracts from fresh leaves and leaf tips incubated in deionised water were measured. The results are means of five replicates and the entire test was repeated at least twice. In each experiment activities of the novel compounds were tested and compared with activity of BAP, which is known to be highly active in wheat senescence assay. The compounds to be tested were dissolved in dimethylsulfoxide (DMSO) and the solution brought up to 10$^{-3}$ M with distilled water. This stock solution was further diluted with the respective media used for the biotest to a concentration ranging from 10$^{-8}$ M to 10$^{-4}$ M. The final concentration of DMSO did not exceed 0.2% and therefore did not affect the biological activity in the assay system used. The IC$_{50}$ values were determined for standard (BAP) and novel tested compounds.

All the tested compounds of the invention exhibit positive effect on delaying of senescence in wheat leaf segments in the dark. All of the newly prepared and tested 1,2,3-thiadiazol-5-yl urea derivatives exceeded the anti-senescent activity of BAP. Importantly, most of the tested 1,2,3-thiadiazol-5-yl urea derivatives of the invention exceeded the anti-senescent activity of BAP at least by one or two orders.

TABLE 2

The effect of novel compounds on delaying of senescence in detached leaf segments of *Triticum aestivum* cv. Hereward in dark conditions

| No | Compound | Senescence bioassay (IC$_{50}$, [µM]/s.d.) | |
|---|---|---|---|
| | 6-benzylaminopurine (BAP) | 155 | (±22) |
| 1 | 1-(2-hydroxy-ethyl)-3-[1,2,3]thiadiazol-5-yl-urea | 26 | (±4.5) |
| 2 | 1-(3-hydroxy-propyl)-3-[1,2,3]thiadiazol-5-yl-urea | 9.1 | (±2.7) |
| 6 | 1-(2-methoxy-ethyl)-3-[1,2,3]thiadiazol-5-yl-urea | 0.95 | (±0.24) |
| 7 | 1-(3-methoxy-propyl)-3-[1,2,3]thiadiazol-5-yl-urea | 11.4 | (±3.8) |
| 8 | 1-(4-methoxy-butyl)-3-[1,2,3]thiadiazol-5-yl-urea | 25.5 | (±5.2) |
| 9 | 1-(5-methoxy-pentyl)-3-[1,2,3]thiadiazol-5-yl-urea | 31 | (±5) |
| 10 | 1-(6-methoxy-hexyl)-3-[1,2,3]thiadiazol-5-yl-urea | 45 | (±11) |
| 16 | 1-(2,2-dimethoxy-ethyl)-3-[1,2,3]thiadiazol-5-yl-urea | 2.9 | (±1.3) |
| 20 | 1-((E)-4-hydroxy-3-methyl-but-2-enyl)-3-[1,2,3]thiadiazol-5-yl-urea | 12.6 | (±4.0) |
| 21 | 1-(3-methyl-but-2-enyl)-3-[1,2,3]thiadiazol-5-yl-urea | 97 | (±15) |
| 25 | 1-(2-hydroxy-propyl)-3-[1,2,3]thiadiazol-5-yl-urea | 3.5 | (±0.6) |
| 28 | 1-(2-methoxy-1-methyl-ethyl)-3-[1,2,3]thiadiazol-5-yl-urea | 8.6 | (±3.5) |
| 34 | 1-(2-thio-ethyl)-3-[1,2,3]thiadiazol-5-yl-urea | 18 | (±4.3) |
| 35 | 1-(3-thio-propyl)-3-[1,2,3]thiadiazol-5-yl-urea | 12 | (±2.9) |
| 39 | 1-(2-methylthio-ethyl)-3-[1,2,3]thiadiazol-5-yl-urea | 3.1 | (±1.1) |
| 42 | 1-(5-methylthio-pentyl)-3-[1,2,3]thiadiazol-5-yl-urea | 10.5 | (±0.9) |
| 50 | 1-allyl-3-[1,2,3]thiadiazol-5-yl-urea | 7.1 | (±2.1) |
| 55 | 1-(prop-2-ynyl)-3-[1,2,3]thiadiazol-5-yl-urea | 22 | (±8.2) |
| 65 | 1-(2-chloro-ethyl)-3-[1,2,3]thiadiazol-5-yhurea | 14 | (±0.8) |
| 75 | 1-(tetrahydro-furan-2-yl-methyl)-3-[1,2,3]thiadiazol-5-yl-urea | 11.2 | (±4.2) |
| 76 | 1-(thiophen-2-yl-methyl)-3-[1,2,3]thiadiazol-5-yl-urea | 32 | (±8) |
| 78 | 1-((5-methyl-furan-2-yl)-methyl)-3-[1,2,3]thiadiazol-5-yl-urea | 45 | (±8.5) |
| 82 | 1-(2-methoxy-ethyl)-1-methyl-3-[1,2,3]thiadiazol-5-yl-urea | 25 | (±3.5) |
| 84 | N-furfuryl-N'-[1,2,3]thiadiazol-5-yl-urea | 1.2 | (±0.3) |

Example 9

Anti-Senescent Activity of Novel Compounds Tested in Senescent Bioassay on Wheat Leaf Segments in the Dark/Light Conditions The ability of the novel compounds to retard chlorophyll degradation in detached wheat leaves was tested also in the light conditions. The experiment was performed as described in Example 7 with modifications as follows—the incubation of the leaves with the compounds was done in the dark/light conditions 8/16 (light—100 µmol·m$^{-2}$·s$^{-1}$) at 22° C. for 7 days. As shown in Table 3, all of the selected novel compounds have shown stronger positive effects to delaying of senescence in wheat leaf segments in dark/light conditions in comparison with BAP. The newly prepared substituted 1,2,3-thiadiazol-5-yl urea derivatives of the invention are much stronger anti-senescent compounds in comparison to the BAP in retarding senescence under optimal (dark/light) conditions.

TABLE 3

The effect of novel compounds on delaying of senescence in detached leaf segments of *Triticum aestivum* cv. Hereward in dark/light conditions

| No. | Compound | Senescence bioassay (IC$_{50}$, µM)/s.d. | |
|---|---|---|---|
| | 6-benzylaminopurine (BAP) | 123 | (±3.3) |
| | TDZ | 1.1 | (±0.2) |
| 2 | 1-(3-hydroxy-propyl)-3-[1,2,3]thiadiazol-5-yl-urea | 0.31 | (±0.1) |
| 6 | 1-(2-methoxy-ethyl)-3-[1,2,3]thiadiazol-5-yl-urea | 0.03 | (±0.02) |
| 7 | 1-(3-methoxy-propyl)-3-[1,2,3]thiadiazol-5-yl-urea | 0.4 | (±0.08) |
| 16 | 1-(2,2-dimethoxy-ethyl)-3-[1,2,3]thiadiazol-5-yl-urea | 0.16 | (±.04) |
| 20 | 1-((E)-4-hydroxy-3-methyl-but-2-enyl)-3-[1,2,3]thiadiazol-5-yl-urea | 0.61 | (±0.22) |
| 25 | 1-(2-hydroxy-propyl)-3-[1,2,3]thiadiazol-5-yl-urea | 0.10 | (±0.02) |
| 28 | 1-(2-methoxy-1-methyl-ethyl)-3-[1,2,3]thiadiazol-5-yl-urea | 0.43 | (±0.03) |
| 50 | 1-allyl-3-[1,2,3]thiadiazol-5-yl-urea | 0.25 | (±0.08) |
| 65 | 1-(2-chloro-ethyl)-3-[1,2,3]thiadiazol-5-yl-urea | 0.7 | (±0.28) |
| 75 | 1-(tetrahydro-furan-2-yl-methyl)-3-[1,2,3]thiadiazol-5-yl-urea | 0.42 | (±0.22) |
| 84 | N-furfuryl-N'-1,2,3-thiadiazol-5-yl-urea | 0.03 | (±0.3) |

Example 10

Protection Against Membrane Lipid Peroxidation in Wheat Under Dark Conditions A typical symptom associated with senescence as a direct consequence of increased reactive oxygen species is membrane lipid peroxidation which produces malondialdehyde (MDA). Therefore the levels of MDA, a decomposition product of lipid peroxidation, were measured in detached wheat leaves that were exposed to the prepared novel derivatives or BAP for four days in the dark as described in Example 7. MDA levels were measured using a thiobarbituric acid (TBA) method. In detail, 100 mg of fresh plant material was homogenized by high speed shaking in a ball mill (MM301, Retsch, Germany) with 1 mL of 70% methanol. The crude extract was centrifuged at 10,000×g for 5 min, and 100 µL aliquot of supernatant was vortexed with 100 µL of 0.5% (w/v) TBA containing 0.1% (w/v) trichloroacetic acid, and the resulting solution was then incubated for 30 min at 95° C. The samples were quickly cooled on ice and centrifuged for 5 min at 1000 g. The absorbance of supernatant was measured at 532 nm with background subtraction at 600 nm and the amount of MDA-TBA complex was calculated from the coefficient of absorbance 155 $mM^{-1}$ $cm^{-1}$.

Novel selected derivatives significantly reduced peroxidation of membrane lipids compared to untreated control and to samples treated with BAP (Table 4—the values express content of MDA, the decomposition product of membrane lipids). The most potent compounds 6 and 74 reduced the level of membrane lipid peroxidation during the dark senescence in the detached wheat leaves to 44.6% and 50.2%, respectively. Interestingly, although BAP strongly delays senescence in detached wheat leaves in the dark, it does not decrease the peroxidation of membrane lipids significantly compared to untreated control. However this fact could explain why BAP is less effective than novel compounds of general formula I in wheat senescence assay.

The newly prepared derivatives of the invention thus had protective function against the negative action of the reactive oxygen species that are highly accumulated in tissues during leaf senescence.

TABLE 4

The effect of novel compounds on lipid membrane peroxidation during the senescence of detached leaves of *Triticum aestivum* cv. Hereward in dark conditions.

| No | Tested compound | MDA (nmol/g FW) |
|---|---|---|
| | Untreated control | 21.5 (±2.8) |
| | 6-benzylaminopurine (BAP) | 19.1 (±1.7) |
| 2 | 1-(3-hydroxy-propyl)-3-[1,2,3]thiadiazol-5-yl-urea | 16.4 (±1.6) |
| 6 | 1-(2-methoxy-ethyl)-3-[1,2,3]thiadiazol-5-yl-urea | 9.6 (±0.7) |
| 7 | 1-(3-methoxy-propyl)-3-[1,2,3]thiadiazol-5-yl-urea | 14.4 (±0.8) |
| 16 | 1-(2,2-dimethoxy-ethyl)-3-[1,2,3]thiadiazol-5-yl-urea | 11.6 (±1.2) |
| 20 | 1-((E)-4-hydroxy-3-methyl-but-2-enyl)-3- | 15.8 (±0.7) |
| 25 | 1-(2-hydroxy-propyl)-3-[1,2,3]thiadiazol-5-yl-urea | 12.6 (±0.83) |
| 28 | 1-(2-methoxy-1-methyl-ethyl)-3-[1,2,3]thiadiazol-5-yl- | 13.9 (±0.9) |
| 50 | 1-allyl-3-[1,2,3]thiadiazol-5-yl-urea | 17.4 (±1.3) |
| 55 | 1-prop-2-ynyl-3-[1,2,3]thiadiazol-5-yl-urea | 14.1 (±1.1) |
| 65 | 1-(2-chloro-ethyl)-3-[1,2,3]thiadiazol-5-yl-urea | 16.4 (±0.5) |
| 75 | 1-(tetrahydro-furan-2-yl-methyl)-3-[1,2,3]thiadiazol-5-yl- | 15.2 (±0.7) |
| 84 | N-furfuryl-N'-1,2,3-thiadiazol-5-yl-urea | 12.7 (±1.1) |

Example 11

1-(2-methoxy-ethyl)-3-[1,2,3]thiadiazol-5-yl-urea (Compound 6) Delays Senescence of Wheat Plants Under Saline Stress Salinity is one of the main problems that negatively affect soil fertility and limit plant growth and production (De Sigmond, A. A. J. 1924. The alkali soils in Hungary and their reclamation. Soil Science 18: 379-381; Richards, L. A. 1954. Origin and nature of saline and alkali soils. pp. 1-6. In: Diagnosis and Improvement of Saline and Alkali Soils. Agricultural Handbook No:60, USDA, Washington, D.C., USA). Under salt stress, physiological drought may occur and excess of salt uptake by plants disrupts cellular functions and damages physiological processes such as photosynthesis and respiration (Leopold, A. C. and R. P Willing. 1984. Evidence for toxicity effects of salt on membranes. pp. 67-76. In: R. C. Staples and G. H. Toenniessen (eds.) Salinity Tolerance in Plants. Strategies for Crop Improvement. A Wiley-Interscience Publication, Toronto, Singapore; Marschner, H. 1995. Mineral nutrition of higher plants. 2nd ed. Academic Press, San Diego, Calif.), which together leads to the stress related senescence of plant organs and may result in plant death.

To investigate the effect of compound 6 to saline-induced senescence seeds of winter wheat, *Triticum aestivum* cv. Hereward, were washed under running water for 24 hours and then sown to 1 L containers on perlite soaked with water or 100 nM water solution of compound 3. Containers were placed in the growth chamber at 25° C. with a 16/8 h light period at 50 $\mu mol \cdot m^{-2} \cdot s^{-1}$. Seven days after planting the plants were treated by 75 mM NaCl solution. Plants were allowed to grow and 25 and 30 days after planting the result was assessed.

Figure 2:
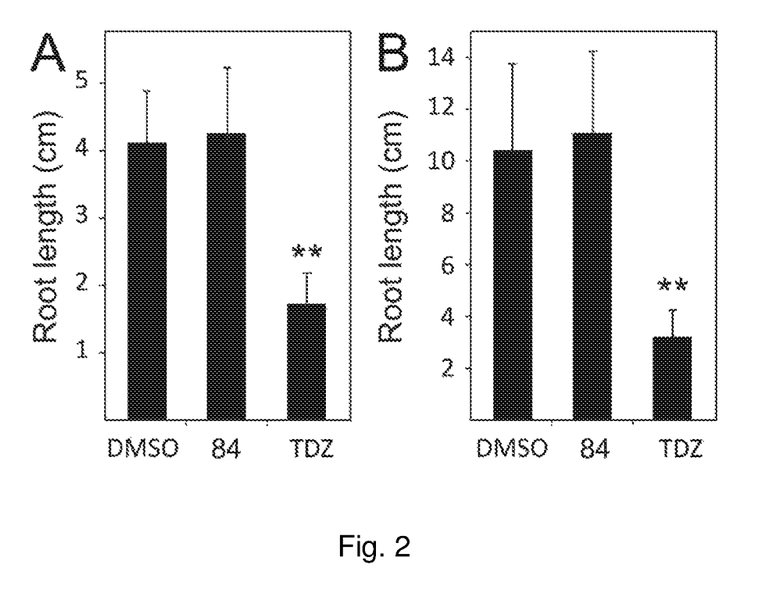
FIG. 2 shows the effect of thidiazurone (comparative compound, TDZ) and N-furfuryl-N'-1,2,3-thiadiazol-5-ylurea (compound 84) on an average length of root of Arabidopsis (A) and wheat Triticum aestivum (B) in root test. In the experiment 0.01% DMSO was used as control and the compounds were used in the concentration of 100 nM. Error bars represent Sd (n=50). Asterisks represent statistically significant differences from the control (Student t-test, two asterisks: p=0.001, one asterisk: p=0.05).

The application of compound 6 can delay the senescence of wheat plants which are grown under saline stress conditions. Picture 2A shows the overall view of young wheat plants 25 days after planting with (right container) and without (left container) application of compound 6. While plants not treated with the compound 6 have first leaf dead and second leaf is yellowing, plants treated with the compound 6 have first leaf yellowing and second leaf green. We have observed that compound 6 significantly delays stress-induced senescence in wheat plants. This in vivo experiment is the proof that compound 6 prolongs the photosynthetic lifespan of wheat, which were exposed to environmental stress.

Example 12

1-(2-methoxy-ethyl)-3-[1,2,3]thiadiazol-5-yl-urea and N-furfuryl-N'-1,2,3-thiadiazol-5-yl-urea Increase Drought Stress Tolerance of Wheat Plants Drought is one of the main problems limiting the growth and production of plants. Drought leads to stress-induced senescence of plant organs, and can result in plant death. Delaying the drought-induced senescence increases life span of stressed plants and their productivity.

To investigate the effect of 1-(2-methoxy-ethyl)-3-[1,2,3]thiadiazol-5-yl-urea and 1-furfuryl-[1,2,3]thiadiazol-5-yl-urea to drought-induced senescence, seeds of winter wheat, *Triticum aestivum* cv. Hereward, were washed under running water for 24 hours and then sown into trays with perlite (30×40 cm) and soaked by water, or 100 nM aqueous solution of 1-(2-methoxy-ethyl)-3-[1,2,3]thiadiazol-5-ylurea or 1-furfuryl-[1,2,3]thiadiazol-5-yl-urea. The trays were placed in a growth chamber at 25° C. with ⅝16 hours light/dark cycle at intensity 100 mol·m$^{-2}$·s$^{1}$. Plants were under drought stress last 20 days. 30 Days after planting it was counted how many plants survived on individual trays.

The result was that the use of 1-(2-methoxy-ethyl)-3-[1,2,3]thiadiazol-5-yl-urea or 1-furfuryl-[1,2,3]thiadiazol-5-yl-urea retarded senescence of wheat plants grown under stress conditions. Plants treated with both urea derivatives are greener (contain more chlorophyll), and have higher survival rate. From plants treated by 1-(2-methoxy-ethyl)-3-[1,2,3]thiadiazol-5-yl-urea or 1-furfuryl-[1,2,3]thiadiazol-5-yl-urea survived 82 and 71% respectively. From untreated plants only 37% plants survived.

This in vivo experiment is clear evidence that 1-(2-methoxy-ethyl)-3-[1,2,3]thiadiazol-5-yl-urea and 1-furfuryl-[1,2,3]thiadiazol-5-yl-urea extended photosynthetic life of wheat plants that have been exposed to environmental stress.

Example 13

1,2,3-Thiadiazol-5-yl-urea Derivatives do not Inhibit Growth of Primary Roots Neither the Formation of Lateral Roots of *Arabidopsis thaliana*

The anti-senescent compounds are known to be negative regulators of root elongation and lateral root formation (Werner, T. et al., *Proc Natl Acad Sci USA* 98, 10487-92, 2001) and their exogenously applied concentrations exceeding 1 M often cause complete inhibition of the root growth.

To investigate in vivo effect of the new derivatives on the root growth and development, seeds of *Arabidopsis thaliana* (wild-type Col-0) were surface sterilized and sown on vertical plates on half-strength Murashige-Skoog medium (supplied with 0.1% sucrose and 6 g/L phytagel) containing 10 nM BAP or 10 nM 1,2,3-thiadiazol-5-yl-urea derivative, or 0.01% DMSO (solvent control). After vernalization (4 days in the dark, 4° C.) plates were transferred into the growth chamber (22° C., 16/8 light/dark). Two weeks after transfer, seedlings were photographed and root elongation and lateral root formation was scored using Scion image software (Scion Corp., Frederick, Md., USA). At least 40 plants were measured for each treatment.

While the roots of the plants that grew in the presence of BAP (table 5 and FIG. 1) were severely and significantly retarded, roots of plants that grew in the presence of 1,2,3-thiadiazol-5-yl-urea derivatives have developed normally (table 6 and 7). Primary root length (table 5) was not significantly shortened by the tested 1,2,3-thiadiazol-5yl-urea derivatives when compared to untreated control as well as the formation of lateral roots (table 5) was not affected. Both root parameters was plus/minus the same or even higher than root parameters of control plants. This indicates that the newly prepared substituted derivatives of the general formula I do not have negative effect on the root growth and development in 10 nanomolar concentrations in contrast to severy inhibitory effect of BAP and can be thus used with advantage for the seeds, seedlings and root treatments in broader concentration range than BAP and without undesirable inhibitory effects.

Figure 1:
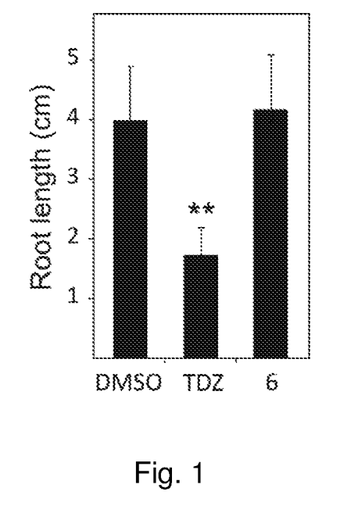
FIG. 1. shows the comparison of the effect of TDZ and 1-(2-methoxy-ethyl)-3-[1,2,3]thiadiazol-5-yl-urea on development of Arabidospsis root. (A) Control treatment with 0.01% DMSO, (B) Treatment by 100 nM TDZ, (C) Treatment by 100 nM 1-(2-methoxy-ethyl)-3-[1,2,3]thiadiazol-5-yl-urea.

In FIG. 1 the effect of 1-(2-methoxy-ethyl)-3-[1,2,3] thiadiazol-5-yl-urea on development of *Arabidospsis* root can be observed.

In FIG. 2, the effect of N-furfuryl-N'-1,2,3-thiadiazol-5-yl-urea on the roots can be observed.

TABLE 5

The effect of novel compounds on the length of primary root and the number of lateral roots of *Arabidopsis thaliana*

| No | Tested compound | Primary root lenght (mm/s.d.) | Lateral root number (±s.d.) |
|---|---|---|---|
| | Untreated control | 42 (±11) | 14 (±8) |
| | 6-benzylaminopurine (BAP) | 15 (±5) | 3.6 (±2) |
| | TDZ | 10 (±4) | 2.1 (±2) |
| 2 | 1-(3-hydroxy-propyl)-3-[1,2,3]thiadiazol-5-yl-urea | 39 (±9) | 12 (±6) |
| 6 | 1-(2-methoxy-ethyl)-3-[1,2,3]thiadiazol-5-yl-urea | 48 (±15) | 17 (±9) |
| 7 | 1-(3-methoxy-propyl)-3-[1,2,3]thiadiazol-5-yl-urea | 40 (±10) | 14 (±10) |
| 16 | 1-(2,2-dimethoxy-ethyl)-3-[1,2,3]thiadiazol-5-yl-urea | 45 (±9) | 19 (±9) |
| 20 | 1-((E)-4-Hydroxy-3-methyl-but-2-enyl)-3- | 32 (±9) | 11 (±6) |
| 25 | 1-(2-hydroxy-propyl)-3-[1,2,3]thiadiazol-5-yl-urea | 35 (±0.8) | 12 (±8) |
| 28 | 1-(2-methoxy-1-methyl-ethyl)-3-[1,2,3]thiadiazol-5-yl- | 41 (±13) | 16 (±7) |
| 50 | 1-Allyl-3-[1,2,3]thiadiazol-5-yl-urea | 42 (±12) | 14 (±10) |
| 55 | 1-Prop-2-ynyl-3-[1,2,3]thiadiazol-5-yl-urea | 40 (±10) | 15 (±8) |
| 65 | 1-(2-chloro-ethyl)-3-[1,2,3]thiadiazol-5-yl-urea | 36 (±8) | 12 (±8) |
| 75 | 1-(tetrahydro-furan-2-yl-methyl)-3-[1,2,3]thiadiazol-5-yl- | 44 (±16) | 17 (±6) |
| 84 | 1-furfuryl-[1,2,3]thiadiazol-5-yl-urea | 30 (±6) | 13 (±6) |

Example 14

Toxicity Towards Human Skin Fibroblasts (BJ Cell Line) Assay

Cytotoxicity of the compounds to human skin fibroblasts (BJ cell line) was determined in a standard Calceinovém AM test. Cells were maintained in plastic tissue culture flasks and grown in Dulbecco's modified Eagle's medium for cell culture (DMEM) at 37° C. in 5% CO$_2$ and 100% humidity. Cells were placed into 96-well microtiter plates (Nunc, Denmark) and after 12 hours pre-incubation, the tested compound was added to a final concentration ranging from 0 to 100 mM. Cells were incubated for 72 hours. At the end of incubation period Calcein AM was added in PBS to a final concentration of 1 g/ml. After 1 hour of incubation fluorescence was measured at 485/538 nm (ex/em wavelength) using Fluoroskan Ascent (Labsystems, Finland). IC$_{50}$ values (the concentration causing reduction of calcein AM conversion to 50%) were calculated from the curves obtained. All experiments were repeated four times with a maximum deviation of 15%. Due to the limited solubility of substances in water, all the tested compounds were dissolved in DMSO and diluted with water to a final concentration.

Using this assay it was found that none of the tested compounds 2, 6, 7, 16, 20, 25, 28, 50, 55, 65, 75, and 84 is toxic to human dermal fibroblasts (BJ cell line), and up to the highest tested concentration of 100 mM. It is believed that the most active compounds will have practical use in agriculture and thus people will be able to manipulate with these compounds. It is therefore highly desirable that this substance is not toxic.

Example 15

1-(2-methoxy-ethyl)-3-[1,2,3]thiadiazol-5-yl-urea (compound 6) and 1-(2-chloro-ethyl)-3-[1,2,3]thiadiazol-5-yl-urea (Compound 65) Increase Number of Tillers and Grain Yield in Field Grown Barley The initial field experiments were done with spring barley (*Hordeum vulgare*), malting variety Bojos in field plots of University of Palacky in Olomouc. All field experiments were done according to criteria for Good Experimental Practices. Six repetitions (each 10 m²) were used per one variant, sowing rate was 3.5 millions of germinated grains per hectare. Field trials were not treated by growth regulators and fungicides, except of applied compounds. Compounds 1-(2-methoxy-ethyl)-3-[1,2,3]thiadiazol-5-yl-urea and 1-(2-chloro-ethyl)-3-[1,2,3]thiadiazol-5-yl-urea were applied once in indicated time (Tillering, BBCH 23-25 or Inflorescence emergence, BBCH 51-53) by foliar spraying in concentration 5 μM. For each variant at least 50 plants were used to obtain morphology parameters. Statistical evaluation was executed in stat. program PAST v. 2.17c.

We have found that both compounds when applied in tillering phase increased number of tillers per plant, compound 6 to 115.7%, compound 65 to 109.2% when compared to control. This led also to an increase in number of spikes per square meter; compound 6 and compound 65 increased this parameter to 110.3% and to 109.2%, respectively. This increase was also responsible for higher grain yield, which was 111.3% in case of compound 6 and 109.3% in case of compound 65. Both compounds also increased grain yield when applied in inflorescence emergence phase, compound 65 to 109.7% and compound 6 to 103.6%. We have further determined the number of grains per spike and the weight of thousand grains after application of compounds 6 and 65. However, these parameters slightly increased (by 2-3%) or remained almost unchanged (Table 6).

TABLE 6

| Timing of application | Control | Compound 6 Tillering, BBCH 23-25 | Compound 6 Inflorescence emergence, BBCH 51-53 | Compound 65 Tillering, BBCH 23-25 | Compound 65 Inflorescence emergence, BBCH 51-53 |
|---|---|---|---|---|---|
| Grain yield (t/ha) | 7.653 | 8.517 | 7.927 | 8.362 | 8.398 |
| % of control | 100 | 111.3 | 103.6 | 109.3 | 109.7 |
| Number of tillers | 4.61 | 5.3* | | 5.0 | |
| % of control | 100 | 115.7* | | 109.2 | |
| Number of grains/spike | 23.49 | 24.27 | 23.37 | 24.42 | 24.17 |
| % of control | 100 | 103.3 | 99.5 | 103.9 | 102.9 |
| Thousand grain weight (g) | 45.85 | 47.18 | 46.77 | 45.35 | 45.96 |
| % of control | 100 | 102.9 | 102.0 | 99.0 | 100.2 |
| Number of spikes/m² | 700.4 | 772.4* | | 764.8* | |
| % of control | 100 | 110.3* | | 109.2* | |

Example 16

1-(2-methoxy-ethyl)-3-[1,2,3]thiadiazol-5-yl-urea (compound 6) and 1-(2-chloro-ethyl)-3-[1,2,3]thiadiazol-5-yl-urea (Compound 65) Increase Grain Yield in Field Grown Barely when Applied in Seed-Coating Mixture Seeds of spring barley (*Hordeum vulgare*), malting variety Bojos were pre-soaked in 50 μM solution of compound 6 or 65 and sown as described in example 15. For each variant at least 50 plants were used to obtain morphology parameters. Statistical evaluation was executed in stat. program PAST v. 2.17c.

Application of both compounds led to the increased grain yield of barley. Compound 6 and 65 increased the yield to 107.3% and to 109.0%, respectively when compared to untreated control.

Example 17

Application of N-furfuryl-N'-1,2,3-thiadiazol-5-yl-urea Increased the Yield of Winter Oilseed Rape in Field Experiments All field experiments were done according to criteria for Good Experimental Practices. Six repetitions (10 m² each) were used per one variant. Field trials were not treated by growth regulators and fungicides, except of applied compound 1-furfuryl-[1,2,3]thiadiazol-5-yl-urea. N-furfuryl-N'-1,2,3-thiadiazol-5-yl-urea was applied once at the precise time (extension growth BBCH 50), by foliar spray at a concentration of 25 μM. For each variant at least 50 plants were used to obtain morphology parameters. Statistical evaluation was executed in stat. program PAST v. 2.17c.

Application of N-furfuryl-N'-1,2,3-thiadiazol-5-yl-urea led to increased seed yield of oilseed rape to 120.9% when compared to the untreated control (Tab. 7). The weight of a thousand kernels (WTK) also increased to 110% over the untreated control (Tab. 7).

TABLE 7

Effect of N-furfuryl-N'-1,2,3-thiadiazol-5-yl-urea (compound 84) application on the yield of winter oilseed rape

| Application | Seed yield (t/ha) | % | WTK (g) | % |
|---|---|---|---|---|
| Control | 4.994 | 100 | 4.35 | 100 |
| Comp. 84 | 6.038 | 120.9 | 4.8 | 110.3 |

Example 18

Application of N-furfuryl-N'-1,2,3-thiadiazol-5-yl-urea Increased the Yield of Spring Barley in Field Experiments During Years 2014 and 2015

All field experiments were done according to criteria for Good Experimental Practices as described in example 17. N-furfuryl-N'-1,2,3-thiadiazol-5-yl-urea was applied once at the precise time (extension growth BBCH 50), by foliar spray at a concentration of 25 μM in a year 2014 and at a concentration of 5 μM in a year 2015. For each variant at least 50 plants were used to obtain morphology parameters. Statistical evaluation was executed in stat. program PAST v. 2.17c. Application of N-furfuryl-N'-1,2,3-thiadiazol-5-yl-urea in both concentration levels resulted in increased seed yield of spring barley to 104.8% and to 106.8% versus the control. WTK remained the same, however, the number of grains per ear was increased to 104.6% versus the control (Tab. 8).

TABLE 8

Effect of N-furfuryl-N'-1,2,3-thiadiazol-5-yl-urea (compound 84) application on yield of spring barely

| Application | Seed yield (t/ha) | % | WTK (g) | % | grains per ear | % |
|---|---|---|---|---|---|---|
| Year 2014 | | | | | | |
| Control | 7.65 | 100 | 45.85 | 100 | 23.5 | 100 |
| Comp. 84 | 8.02 | 104.8 | 45.88 | 100.06 | 24.6 | 104.6 |
| Year 2015 | | | | | | |
| Control | 7.01 | 100 | | | | |
| Comp. 84 | 7.49 | 106.8 | | | | |

Example 19

Ethylene Production (Defoliating Activity) Assay

TDZ is largely used in USA as a cotton defoliant (Arndt F, R Rusch, H V Stilfried, 1976, SN 49537, A new cotton defoliant. Plant Physiol 57: S-99), because it stimulates plants to produce high amounts of ethylene (Suttle JC, 1983, Effect of the defoliant thidiazuron on ethylene production. Plant Physiol 72: S-121; Suttle JC, 1984, Effect of the defoliant thidiazuron on ethylene evolution from Mung Bean Hypocotyl Segments, Plant. Physiol. 75:902-907). Ethylene is known to be an endogenous regulator of senescence and abscission in many plants. (Addicott FT 1982 Abscission. Univ. of California Press, Berkeley; Nooden LD, AC Leopold 1978 Phytohormones and the endogenous regulation of senescence and abscission. In DS Letham, P B Goodwin, T J V Higgins, eds, Phytohormones and Related Compounds: A Comprehensive Treatise. Elsevier/North Holland, Amsterdam, pp 329-370).

We investigated the effect of the compounds of the invention on ethylene production in wheat leaves. The leaves were obtained as described in Example 8, placed in 5 mL glass vials and immersed at 10 μM solutions of tested compounds of the invention or TDZ. Distilled water was used as a control treatment. After 96 h incubation in the dark at 25° C., 1 mL of air was taken from the vials and content of ethylene in it was determined using gas chromatography with the flame ionization detector (GC-FID) method described by Fišerová et al. (Fišerová H, Kula E, Klemš M, Reinöhl V (2001) Phytohormones as indicators of the degree of damage in birch (*Betula pendula*). *Biológia* 56: 405-409).

Contrary to TDZ, compounds related to this invention do not induce ethylene production in wheat leaf tissues with such potency as TDZ. While tested compounds elevated the production of ethylene by maximum of 25% (compound 84) compared to untreated control, TDZ elevated production of ethylene in wheat leaves by 133%. Thidiazuron thus causes at least 5 times higher production of ethylene than the novel tested compounds. Generally, most of the tested compounds did not increase ethylene production significantly when compared to untreated control. Some of the novel compounds even showed inhibition of ethylene evolution (compounds 20 and 28) when compared to control (Table 9).

TABLE 9

| No. | Compound | Ethylene produced nL/g FW (±s.d.) |
|---|---|---|
| | Control | 270 (±15) |
| | TDZ | 628 (±45) |
| 2 | 1-(3-hydroxy-propyl)-3-[1,2,3]thiadiazol-5-yl-urea | 293 (±21) |
| 6 | 1-(2-methoxy-ethyl)-3-[1,2,3]thiadiazol-5-yl-urea | 275 (±14) |
| 7 | 1-(3-methoxy-propyl)-3-[1,2,3]thiadiazol-5-yl-urea | 312 (±18) |
| 16 | 1-(2,2-dimethoxy-ethyl)-3-[1,2,3]thiadiazol-5-yl-urea | 267 (±23) |
| 20 | 1-((E)-4-hydroxy-3-methyl-but-2-enyl)-3-[1,2,3]thiadiazol-5-yl-urea | 254 (±22) |
| 25 | 1-(2-hydroxy-propyl)-3-[1,2,3]thiadiazol-5-yl-urea | 281 (±31) |
| 28 | 1-(2-methoxy-1-methyl-ethyl)-3-[1,2,3]thiadiazol-5-yl-urea | 246 (±12) |
| 50 | 1-allyl-3-[1,2,3]thiadiazol-5-yl-urea | 279 (±18) |
| 65 | 1-(2-chloro-ethyl)-3-[1,2,3]thiadiazol-5-yl-urea | 335 (±25) |
| 75 | 1-(tetrahydro-furan-2-yl-methyl)-3-[1,2,3]thiadiazol-5-yl-urea | 282 (±19) |
| 84 | N-furfuryl-N'-1,2,3-thiadiazol-5-yl-urea | 337 (±28) |

Example 20

Preparations

The preparations usually contain from 0.1 to 99% (w/w), preferably 0.1 to 95% (w/w), of active ingredient mixture comprising a compound of formula (I), from 1 to 99.9% (w/w) of a solid or liquid adjuvant, and from 0.1 to 25% (w/w) of a surfactant. Whereas commercial products are usually formulated as concentrates, the end user will normally employ dilute formulations. The preparations may also comprise further ingredients, such as stabilisers, e.g. vegetable oils or epoxidised vegetable oils (epoxidised coconut oil 0.1, rapeseed oil or soybean oil), antifoams, e.g. silicone oil, preservatives, viscosity regulators, binders, tackifiers, and also fertilisers or other active ingredients. Preferred preparations have especially the following compositions: (%=percent by weight)

Formulations

Active ingredient mixture comprising a compound or mixture of compounds of formula (I) (=active ingredient mixture).

| A1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | 2% | — | 2% | — |
| cyclohexanone | — | — | 10% | 20% |
| arom. hydrocarbon mixture $C_9$-$C_{12}$ | 83% | 82% | 53% | 18% |

Emulsions of any desired concentration can be obtained from such concentrates by dilution with water.

| A2. Solutions | a) | b) | c) | d) |
|---|---|---|---|---|
| active ingredient mixture | 5% | 10% | 50% | 90% |
| 1-methoxy-3-( 3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$-$C_{12}$ | 75% | 60% | — | — |

The solutions are suitable for use in the form of microdrops.

| A3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | 1% | 2% | — | — |
| highly dispersed silicic acid | 1% | 3% | 5% | 10% |
| kaolin | 87% | 61% | 37% | — |

The active ingredient is mixed thoroughly with the adjuvants and the mixture is thoroughly ground in a suitable mill, affording wettable powders which can be diluted with water to give suspensions of any desired concentration.

| A4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (.AE 0.1-1 mm) e.g. CaCO$_3$ or SiO$_2$ | 99.0% | 93% | 83% |

The active ingredient is dissolved in methylene chloride and applied to the carrier by spraying, and the solvent is then evaporated off in vacuo.

| A5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (AE 0.1-1 mm) e.g. CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| A6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97% | 93% | 90% | 79% |

The active ingredient is mixed and ground with the adjuvants, and the mixture is moistened with water. The mixture is extruded and then dried in a stream of air.

| A7. Dusts | a) | b) | c) |
|---|---|---|---|
| active ingredient mixture | 0.1% | 1% | 5% |
| talcum | 39.9% | 49% | 35% |
| kaolin | 60% | 50% | 60% |

Ready-to-use dusts are obtained by mixing the active ingredient with the carriers and grinding the mixture in a suitable mill.

| A8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | 1% | 2% | — | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 86% | 78% | 64% | 38% |

The finely ground active ingredient is intimately mixed with the adjutants, giving a suspension concentrate from which suspensions of any desired concentration can be obtained by dilution with water.

The invention claimed is:

1. A 1,2,3-thiadiazol-5-yl-urea derivative of the formula (Ia),

Ia wherein
R1a is selected from the group consisting of:
$C_1$-$C_6$ alkyl, substituted with at least one moiety selected from hydroxy, thio, cyano and halogen;
$C_2$-$C_6$ alkenyl, optionally substituted with at least one moiety selected from hydroxy, $C_1$-$C_4$ alkoxy, thio, $C_1$-$C_4$ alkylthio, cyano and halogen;
$C_2$-$C_6$ alkynyl, optionally substituted with at least one moiety selected from hydroxy, $C_1$-$C_4$ alkoxy, thio, $C_1$-$C_4$ alkylthio, cyano and halogen;
tetrahydro-furan-2-yl-methyl or tetrahydro-furan-3-yl-methyl, optionally substituted with at least one moiety selected from hydroxy, $C_1$-$C_4$ alkyl, $C_1$-$C_4$ alkoxy, thio, $C_1$-$C_4$ alkylthio, cyano and halogen;
thiophen-2-yl-methyl or thiophen-3-yl-methyl, optionally substituted with at least one moiety selected from hydroxy, $C_1$-$C_4$ alkyl, $C_1$-$C_4$ alkoxy, thio, $C_1$-$C_4$ alkylthio, cyano and halogen;
furan-2-yl-methyl or furan-3-yl-methyl, substituted with at least one moiety selected from hydroxy, $C_1$-$C_4$ alkyl, $C_1$-$C_4$ alkoxy, thio, $C_1$-$C_4$ alkylthio, cyano and halogen;
1,3-dioxolan-2-yl-methyl, optionally substituted with at least one moiety selected from hydroxy, $C_1$-$C_4$ alkyl, $C_1$-$C_4$ alkoxy, thio, $C_1$-$C_4$ alkylthio, cyano and halogen;
tetrahydropyran-2-ylmethyl, tetrahydropyran-3-ylmethyl or tetrahydropyran-4-ylmethyl, optionally substituted with at least one moiety selected from hydroxy, $C_1$-$C_4$ alkyl, $C_1$-$C_4$ alkoxy, thio, $C_1$-$C_4$ alkylthio, cyano and halogen; and
(3,4-dihydro-2H-pyran-2-yl)methyl, (3,4-dihydro-2H-pyran-3-yl)methyl, (3,4-dihydro-2H-pyran-4-yl)methyl, (3,4-dihydro-2H-pyran-5-yl)methyl or (3,4-dihydro-2H-pyran-6-yl)methyl, optionally substituted with at least one moiety selected from hydroxy, $C_1$-$C_4$ alkyl, $C_1$-$C_4$ alkoxy, thio, $C_1$-$C_4$ alkylthio, cyano and halogen.

2. A method of inhibiting stress symptoms in plant tissue, the plant tissue comprising at least one of plants, plant organs, and plant cells which are subjected to stress conditions, said method comprising applying at least one 1,2,3-thiadiazol-5-yl-urea derivative of the formula (Ia) according to claim 1 to plant tissue in need thereof.

3. The method according to claim 2, the method comprising identifying plant tissue subjected to at least one stress condition selected from dryness, excessive heat, cold, and high salinity, and then in response applying the compound of formula (Ia) to said plant tissue to inhibit effects of said stress.

4. The method according to claim 2, wherein the plant tissue is being grown in tissue culture, and wherein the compound of formula (Ia) is provided to said plant tissue in tissue culture.

5. The method according to claim 2, wherein the plant tissue comprises field crop plants, and wherein the compound of formula (Ia) is applied to the field crop plants in an agricultural field to inhibit symptoms of stress.

6. A method of inhibiting senescence in plant tissue, the plant tissue including at least one of plants, plant organs, and plant cells, the method comprising applying at least one 1,2,3-thiadiazol-5-yl-urea derivative of formula (Ia) according to claim 1 to plant tissue in need thereof.

7. The method according to claim 6, the method comprising identifying plant tissue subjected to at least one stress condition selected from dryness, excessive heat, cold, and high salinity, and then in response applying the compound of formula (Ia) to said plant tissue.

8. The method according to claim 6, wherein the plant tissue is being grown in tissue culture, and wherein the compound of formula (Ia) is provided to said plant tissue in tissue culture.

9. The method according to claim 6, wherein the plant tissue comprises field crop plants, and wherein the compound of formula (Ia) is applied to the field crop plants in an agricultural field to inhibit senescence thereof.

10. A method of preparation of the compounds of formula (Ia) according to claim 1, wherein 1,2,3-thiadiazol-5-ylisocyanate is prepared from 1,2,3-thiadiazol-5-ylamine and diphosgene, and then further reacted with a corresponding amine of formula $R_{1a}NH_2$, wherein $R_{1a}$ is as defined in claim 1.

11. A method of increasing yield in plants, the method comprising applying at least one 1,2,3-thiadiazol-5-yl-urea derivative of formula (Ia) according to claim 1 to said plants.

12. The method of increasing yield in plants of claim 11, wherein said plants are field crops, the method comprising applying at least one compound of formula (Ia) to said field crops to increase yield.

13. The method of increasing yield in plants of claim 11, wherein the compound of formula (Ia) is applied to seeds, and the seeds are subsequently planted.

14. The method of increasing yield in plants of claim 11, wherein the compound of formula (Ia) is delivered to the plants by application to a seed furrow as a pre-emergence application.

15. The method of increasing yield in plants of claim 11, wherein the compound of formula (Ia) is delivered to the plants by foliar application.

16. The method of increasing yield in plants of claim 11, wherein the plants are grain crops, and the compound of formula (Ia) increases grain yield in said grain crops.

17. The method of increasing yield in plants of claim 11, wherein said plants are field crops, and wherein the compound of formula (Ia) is applied as a preparation in combination with at least one of a fertilizer and a micronutrient supplement.

18. The method of increasing yield in plants of claim 11, wherein said plants are being grown in a tissue culture, the method comprising applying at least one compound of formula (Ia) to said plants in tissue culture to increase growth yield of the plants.

* * * * *